United States Patent
Suzuki et al.

(10) Patent No.: US 7,956,995 B2
(45) Date of Patent: Jun. 7, 2011

(54) OPTICAL SENSOR AND METHOD FOR MANUFACTURING THE SAME

(75) Inventors: Motofumi Suzuki, Kyoto (JP); Takao Fukuoka, Joyo (JP)

(73) Assignee: Kyoto University, Kyoto (JP)

( * ) Notice: Subject to any disclaimer, the term of this patent is extended or adjusted under 35 U.S.C. 154(b) by 963 days.

(21) Appl. No.: 11/794,543

(22) PCT Filed: Dec. 28, 2005

(86) PCT No.: PCT/JP2005/024100
§ 371 (c)(1),
(2), (4) Date: Jul. 2, 2007

(87) PCT Pub. No.: WO2006/073117
PCT Pub. Date: Jul. 13, 2006

(65) Prior Publication Data
US 2009/0279084 A1    Nov. 12, 2009

(30) Foreign Application Priority Data
Jan. 7, 2005 (JP) .................. 2005-003019

(51) Int. Cl.
G01J 3/44    (2006.01)
B23P 19/04   (2006.01)
C12M 3/00    (2006.01)

(52) U.S. Cl. ................ 356/301; 435/287.6; 29/460

(58) Field of Classification Search .......... 356/300–301, 356/309–311, 317–318; 435/287.6, 299.2, 435/283.1, 309.4; 29/460
See application file for complete search history.

(56) References Cited

U.S. PATENT DOCUMENTS

| 4,448,485 | A | 5/1984 | Bergman et al. |
| 5,017,007 | A | 5/1991 | Milne et al. |
| 6,538,042 | B1 * | 3/2003 | Berghmans et al. ............ 521/58 |
| 6,623,970 | B1 * | 9/2003 | Willson, III ..................... 506/4 |
| 6,770,353 | B1 * | 8/2004 | Mardilovich et al. ......... 428/209 |
| 7,019,828 | B2 * | 3/2006 | Su et al. ........................ 356/301 |
| 7,022,617 | B2 * | 4/2006 | Subramanian et al. ....... 438/719 |
| 7,322,871 | B2 * | 1/2008 | Lambertini et al. ............ 445/48 |

(Continued)

FOREIGN PATENT DOCUMENTS

JP    WO 01/25757 A1    4/2001

(Continued)

OTHER PUBLICATIONS

J. C. Hulteen et al., "Nanosphere Lithography: Size-Tunable Silver Nanoparticle and Surface Cluster Arrays," J. Phys. Chem. B vol. 103, 1999, pp. 3854-3863.

(Continued)

Primary Examiner — Sang Nguyen
(74) Attorney, Agent, or Firm — Oliff & Berridge, PLC (57) ABSTRACT

An optical sensor according to the present invention significantly enhances the sensitivity of an optical sensor for molecular measurement using light such as Surface Enhanced Raman Scattering and Plasmon Resonance Spectroscopy utilizing the local plasmon's excitation of a noble metal. By using a transparent substance deposition step for forming a large number of anisotropic nano-columns having a predetermined aspect ratio, with their longitudinal direction and transverse direction aligned, by depositing a transparent substance onto a substrate from an oblique position while periodically inverting the position and a noble metal deposition step for depositing a noble metal onto surfaces of the formed anisotropic nano-columns, it is possible to manufacture an optical sensor with very high sensitivity at very low cost.

6 Claims, 8 Drawing Sheets

U.S. PATENT DOCUMENTS

| | | | |
|---|---|---|---|
| 7,411,680 B2 * | 8/2008 | Chang et al. | 356/432 |
| 7,419,820 B2 * | 9/2008 | Watanabe et al. | 435/287.6 |
| 7,460,224 B2 * | 12/2008 | Wang et al. | 356/301 |
| 7,521,851 B2 * | 4/2009 | Tolt | 313/311 |
| 7,655,457 B2 * | 2/2010 | Kuwabara et al. | 435/299.2 |
| 2004/0125266 A1 * | 7/2004 | Miyauchi et al. | 349/57 |
| 2005/0105085 A1 | 5/2005 | Naya | |
| 2006/0055922 A1 * | 3/2006 | Li et al. | 356/301 |
| 2007/0177139 A1 * | 8/2007 | Kamins et al. | 356/301 |

FOREIGN PATENT DOCUMENTS

| | | |
|---|---|---|
| JP | A 2002-372620 | 12/2002 |
| JP | A 2003-511666 | 3/2003 |
| JP | A 2004-170334 | 6/2004 |
| JP | A 2005-172569 | 6/2005 |
| JP | A 2005-219184 | 8/2005 |

OTHER PUBLICATIONS

P. F. Liao et al., "Surface-Enhanced Raman Scattering From Microlithographic Silver Particle Surfaces," Chemical Physics Letters, vol. 82, No. 2, Sep. 1981, pp. 355-359.

Foreign Office Action mailed Mar. 15, 2011 issued in Japanese Application No. 2006-550853 (with translation).

* cited by examiner

IN-PLANE INVERSION

EVAPORATION SOURCE        EVAPORATION SOURCE

OPTICAL SENSOR AND METHOD FOR MANUFACTURING THE SAME

TECHNICAL FIELD

The present invention relates to an optical sensor used for molecular measurement and a method for manufacturing this sensor.

BACKGROUND ART

In recent years, there have been numerous studies on optical sensors for analyzing molecules with light. These studies include; Surface Enhanced Raman Scattering for enhancing the sensitivity of Raman scattering by local field enhancement which occurs when a local plasmon is excited in a noble metal such as Au and Ag; and Surface Plasmon Resonance Spectroscopy using the properties in which a resonant frequency of a local plasmon is sensitive to the environmental permittivity.

When a molecular measurement is generally performed with an optical sensor, a liquid solution which contains a substance to be targeted is dropped on the surface of the sensor, and probe light is incident under the conditions (e.g. kind, intensity and incident angle of the light) according to a measurement method. The reflected or scattered light is received by a light detector and is analyzed to measure (identify) the substance. If the measurement sensitivity of these optical sensors is increased to single-molecule level, it is expected that the sensors can be applied in many fields such as medical fields, biotechnologies and environments.

Controlling the shape and alignment of noble metal nanoparticles is the key to enhancing the sensitivity of a sensor which is used for molecular measurement with light. Since surface charge which enhances the local field appears on the edges of nanoparticles, if the control can be accomplished properly, the measurement sensitivity will be improved dramatically. In addition, to make the sensor available as a practical product, the sensor is required to not only have high sensitivity but also to simultaneously have high reproducibility and to be inexpensive to manufacture.

Conventionally, many technologies aimed at obtaining a sensor which meets the previously described conditions have been developed and disclosed. For example, Non-Patent Document 1 discloses a nanosphere lithography method as a method for manufacturing a substrate for Surface Enhanced Raman scattering. With this method, it is possible to align triangular nanoparticles regularly so that their apexes are facing each other by a relatively simple procedure, and highly-sensitive molecular measurement can be therefore performed with this substrate. However, the local field enhancement with this technology has a limitation attributable to the triangular shape of the nanoparticles.

Additionally, as one of the technologies regarding Raman scattering measurement sensor, Patent Document 1 discloses a sensor and the method for making this sensor in which particles having the same diameter and dimension whose surfaces are coated with metal are repeatedly aligned so as to form periodic irregularity on the surface of a particle layer. This sensor has uniformity and high reproducibility, and can be manufactured easily and inexpensively. Nonetheless, because the shape of the particles is spherical, the measurement sensitivity is not yet sufficient.

Holography and electron lithography are other methods for controlling the shape and alignment of nanoparticles. With these methods, it is possible to align regularly nanometer-scale particles (see Patent Document 3 and Non-Patent Document 2 for examples).

Unfortunately, these methods are impractical as a method for manufacturing disposable sensors for molecular measurement because the products are too expensive.

Patent Document 4 also discloses a technology regarding a substrate for Surface Enhanced Raman Scattering: a substrate utilizing a needle-like column structure which is obliquely adhered to the substrate by obliquely depositing a metal to the substrate. With this method, it is possible to form nanometer-scale self-assembled elongated metal nanorods; however, since the needle-like columns are not aligned with their edges facing each other, the enhancing effect is limited.

[Patent Document 1] Unexamined Japanese Patent Publication No. 2004-170334
[Patent Document 2] Unexamined Japanese Patent Publication No. 2002-372620
[Patent Document 3] U.S. Pat. No. 4,448,485
[Patent Document 4] U.S. Pat. No. 5,017,007
[Non-Patent Document 1] John C. Hulteen et al. "Nanosphere Lithography: Size-Tunable Silver Nanoparticle and Surface Cluster Arrays", J. Phys. Chem. B, 103, 3854-3863 (1999)
[Non-Patent Document 2] P. F. Liao et al. "Surface-enhanced raman scattering from microlithographic silver particle surfaces", Chemical Physics Letters Volume 82, number 2, 1 Sep. 1981

DISCLOSURE OF THE INVENTION

Problem to be Solved by the Invention

The objective of the present invention is to provide an optical sensor which has dramatically high measurement sensitivity compared to conventional sensors, and additionally has reproducibility. The present invention also provides an easy method for manufacturing the optical sensor.

The inventors of this invention had been dedicated to solving the problems described earlier and discovered that the characteristic structure of the polarization controlling element, which is disclosed in Patent Document 2, significantly enhances a local field, and also found out that by using this polarization controlling element as an optical sensor, it is possible to perform molecular measurement with extremely high sensitivity. Furthermore, the inventors discovered a method for manufacturing the element very easily and inexpensively.

Means for Solving the Problem

A method for manufacturing an optical sensor, which is provided in order to solve the previously-described problem, includes the steps of:

a transparent substance deposition step for depositing a transparent substance onto a substrate from an oblique direction while periodically inverting the direction to form a large number of anisotropic nano-columns having a predetermined aspect ratio, with their longitudinal direction and transverse direction aligned; and a noble metal deposition step for depositing a noble metal onto surfaces of the formed anisotropic nano-columns.

Effect of the Invention

In an optical sensor according to the present invention, the cross section of a noble metal portion, which forms a portion of each nano-column, taken substantially parallel to the substrate has an elongated shape. Therefore, it resonates with a light of a certain wavelength, and a strong local field is likely to be generated at the edges of the longitudinal direction of the noble metal portion. In addition, since a large number of nano-columns are oriented with their longitudinal directions aligned, edges of the noble metal portions of each nano-column are close, and such adjacent spots are abundant. Therefore, the electric field enhancement is remarkable. As a result of these conditions, the sensitivity of an optical molecular measurement is significantly high.

Furthermore, since spaces are formed between a large number of nano-columns which are formed on the substrate, a liquid to be measured can easily flow into the spaces.

The method for manufacturing an optical sensor according to the present invention is simple in that it includes depositing a transparent substance or a noble metal onto a plate substrate from an oblique direction while alternately inverting the direction. Thus, it has high reproducibility and the manufacturing cost is inexpensive.

Moreover, with the method for manufacturing an optical sensor of the present invention, the shapes of nano-columns are not uniformly equal as manufactured by general conventional lithography methods, but vary moderately. Accordingly, incident light and scattering light resonate preferably, and this leads to an advantage that a higher enhancement effect is achieved.

Furthermore, in the optical sensor according to the present invention, the nano-columns locations (i.e. edges of the noble metal portion) are in close proximity, within several nanometers. This structure enhances the local field, and the Raman scattering enhancement increases dramatically. It is extremely difficult to make the structure where nano-columns are close to this extent by conventional holography or lithography.

EXPLANATION OF NUMERALS

1 . . . Optical Sensor
2 . . . Substrate
3 . . . Nano-Column
31 . . . Transparent Portion
32 . . . Noble Metal Portion
4 . . . Incident Light Portion
5 . . . Light Monitor
6 . . . Rotation Controller
7 . . . Quarter Wavelength Plate
8 . . . Mirror

BEST MODES FOR CARRYING OUT THE INVENTION

Figure 1:
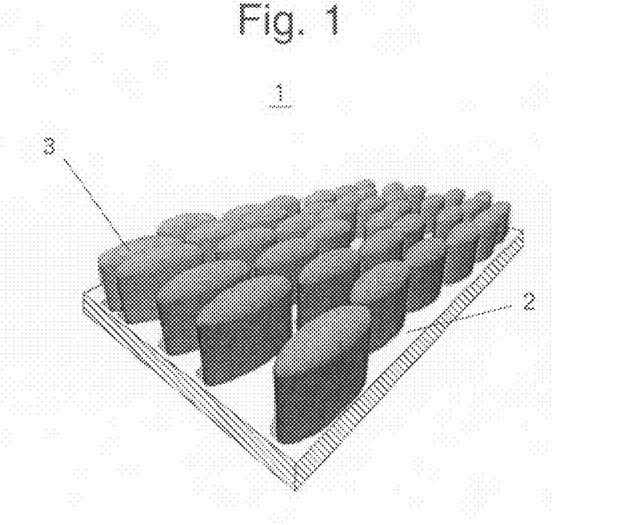
FIG. 1 is a schematic view of an optical sensor of the present invention.

An optical sensor 1 according to the present invention is structured with, as shown in FIG. 1, a large number of nano-columns 3 whose cross section taken substantially parallel to the substrate has a certain aspect ratio (elongated shape) are formed on a substrate 2 to be oriented along one direction.

The substrate 2 is a flat plate for having a large number of nano-columns formed on its surface. It is possible to use various kinds of glass, semiconductors, and metals as a material of the substrate, but the selected material should be suitable for an optical measurement. For example, when performing a molecular measurement by surface plasmon resonance spectroscopy, a prism made of glass can be the substrate, or a material of a transparent glass plate and a prism adhered together can also be the substrate.

The surface of the substrate 2 may be flat, but it can be prepared mechanically or chemically so that the nano-columns develop easily. Or, it is possible to perform a rubbing treatment on the surface of the substrate 2 with pre-heated polyimide or Teflon (registered trademark) or to form tiny grinding marks so that a nano-column 3 becomes more isotropic.

Figure 2:
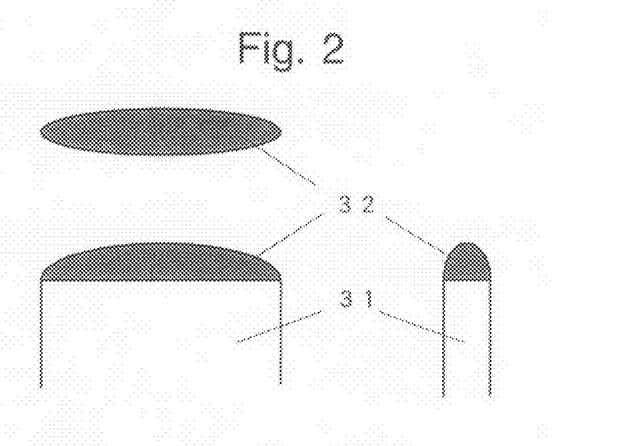
FIG. 2 is an example of a nano-column.

The nano-column 3 comprises a combination of a transparent portion 31 made of a transparent substance and a noble metal portion 32 made of a noble metal (FIG. 2). Typically, at least one or more layers of the noble metal portion 32 are formed on the surface or inside of the transparent portion 31, although configuration examples will be described later.

The material of the transparent portion 31 can be anything as long as it is transparent to probe light; however, it is necessary to select one in which plasma resonance does not occur at the wavelength of the probe light to be used because the permittivity of a material affects its plasma resonance frequency. For example, it is preferable to use an oxide such as $SiO_2$, $Ta_2O_5$, and $TiO_2$, and a fluoride such as LiF.

The noble metal portion 32 can be composed of a simple substance or an alloy of various kinds of noble metals. However, it is preferable to use either Au, Ag, or Cu in order to obtain a highly-sensitive optical sensor.

The shape of the nano-column 3 is now described. The nano-column 3 has an anisotropic shape elongated along the direction which is parallel to the surface of the substrate 2.

Preferably, the length of the longitudinal length may be short enough not to be significantly affected by the scattering of the probe light, and also correspond to the resonant frequency of the probe light. If the aspect ratio, a ratio of the longitudinal length to the transverse length, is two or more, the transparent property along the light axis of an incident light differs according to the anisotropic nature of the shape of the nano-column.

Although it is preferable that the nano-column 3 stand upright at a right angle to the surface of the substrate 2, it can be slightly tilted. The distance between the nano-columns 3 must be short enough not to be significantly affected by the scattering of the probe light. The adjacent nano-columns 3 can be touching each other.

Such nano-columns can be preferably manufactured by the oblique deposition technique which will be described later.

Some configuration examples of the transparent portion 31 and the noble metal portion 32 will be described in reference to FIG. 2 through FIG. 11. In these figures, the upper left portion is a plain view from above the nano-column 3, the lower left portion is a side view in longitudinal direction, and the lower right portion is a side view in the transverse direction.

Configuration Example 1

Figure 3:
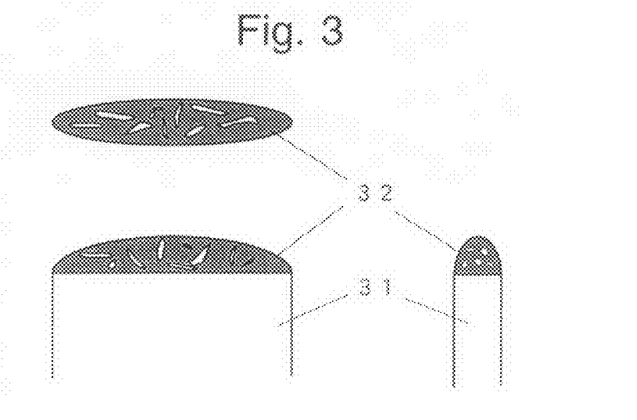
FIG. 3 is another example of a nano-column.

The noble metal portion 32 is formed on top of the nano-column 3 (FIG. 2). This configuration can be obtained by depositing a noble metal while properly changing the angle of the substrate 2 after the nano-columns 3 are formed. In this example, the noble metal portion 32 may be inhomogeneously formed as shown in FIG. 3.

Configuration Example 2

Figure 4:
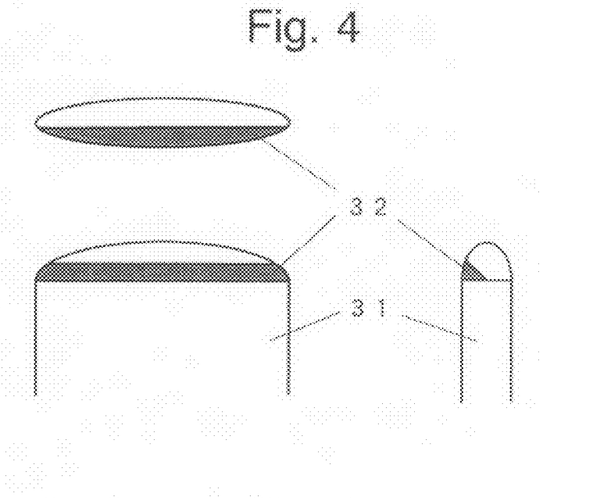
FIG. 4 is another example of a nano-column.
Figure 5:
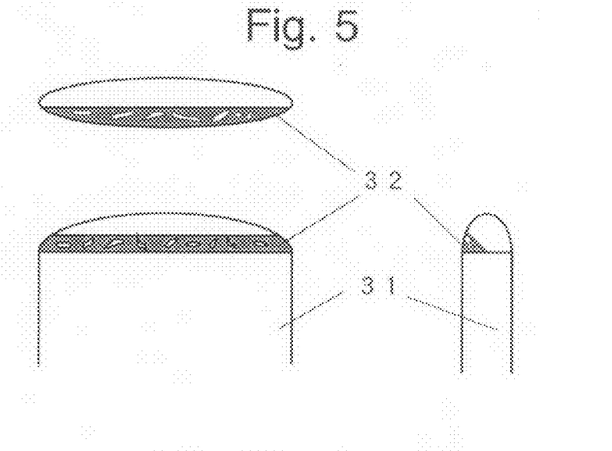
FIG. 5 is another example of a nano-column.

The noble metal portion 32 is partially formed on top of the nano-column 3 (FIG. 4). This configuration can be obtained by performing an oblique deposition from one direction to the transparent portion 31. In this example, the noble metal portion 32 may be inhomogeneously formed as shown in FIG. 5.

Configuration Example 3

Figure 6:
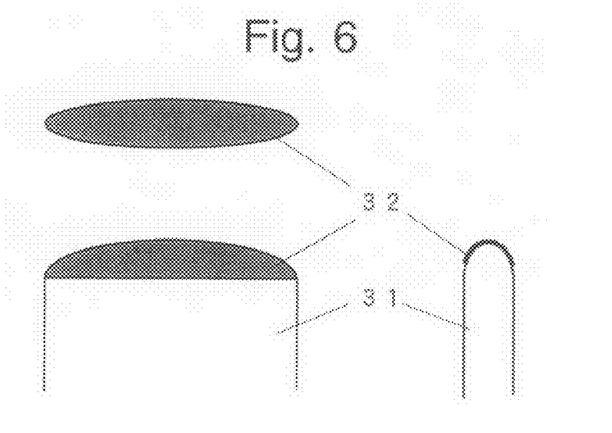
FIG. 6 is another example of a nano-column.
Figure 7:
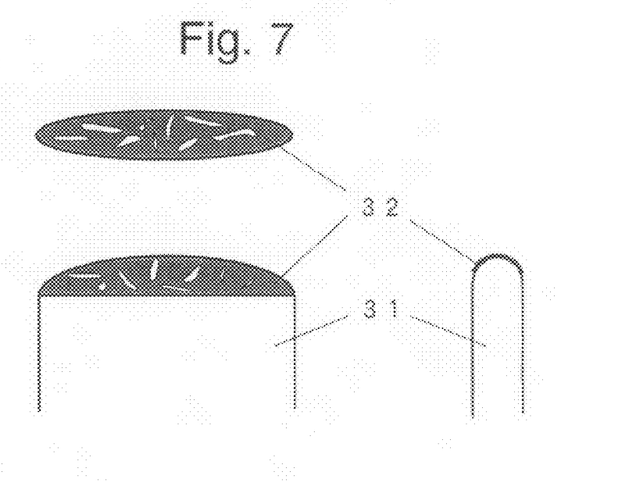
FIG. 7 is another example of a nano-column.

Only the top of the nano-column 3 is covered with the noble metal portion 32 (FIG. 6). This configuration can be obtained by the aforementioned configuration example 1 with less noble metal deposition amount. In this example, the noble metal portion 32 may be inhomogeneously formed as shown in FIG. 7.

Configuration Example 4

Figure 8:
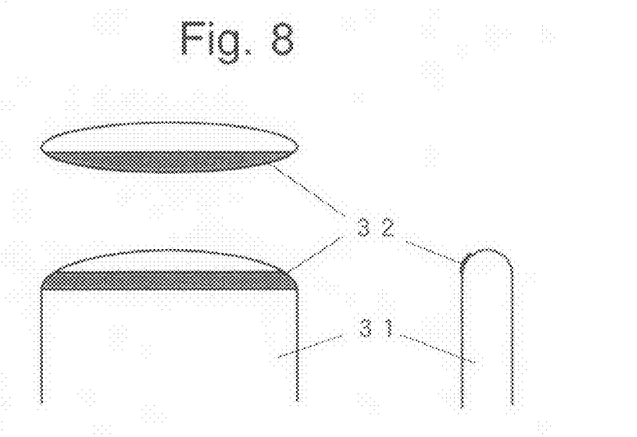
FIG. 8 is another example of a nano-column.
Figure 9:
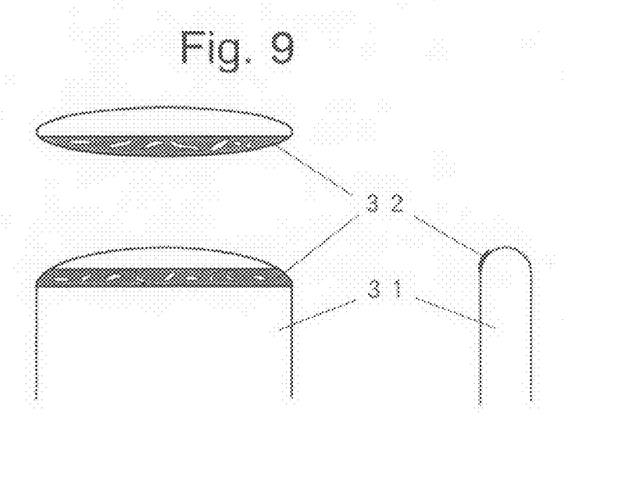
FIG. 9 is another example of a nano-column.

A portion of the top of the nano-column 3 is covered with the noble metal portion 32 (FIG. 8). This configuration can be obtained by the aforementioned configuration example 2 with less noble metal deposition amount. In this example, the noble metal portion 32 may be inhomogeneously formed as shown in FIG. 9.

Configuration Example 5

Figure 10:
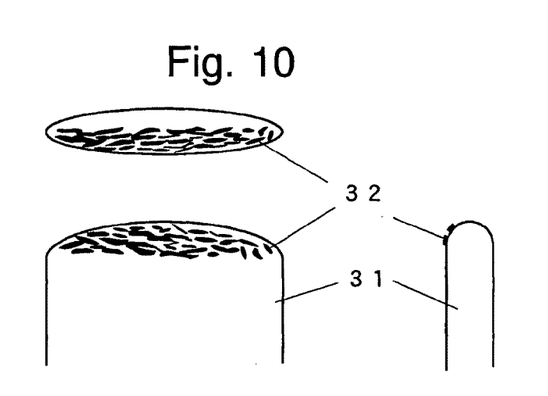
FIG. 10 is another example of a nano-column.

The noble metal portions 32 in the configuration examples 1 thorough 4 are formed with noble metal particles (FIG. 10). The distance between each particle is preferably close enough to interact with each other.

Configuration Example 6

Figure 11:
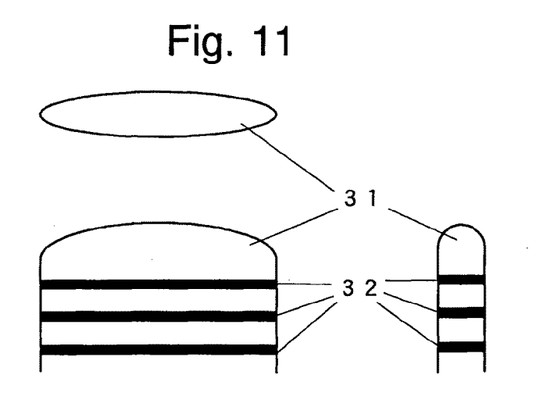
FIG. 11 is another example of a nano-column.

A multilayer structure in which the transparent portions 31 and the noble metal portions 32 are alternately formed (FIG. 11). With this configuration, it is possible to detect only molecules which penetrate between the nano-columns, i.e. a porous material, without being influenced by large pieces of dirt. In addition, it has an advantage in that the sensitivity increases as more noble metal portions (sensitive portions) are formed. In this case, the gap between each noble metal portion 32 may preferably be 10 nm or more with transparent portions 31 in order to prevent the noble metals from touching or interacting with each other and consequently decreasing the effective anisotropy.

Figure 13:
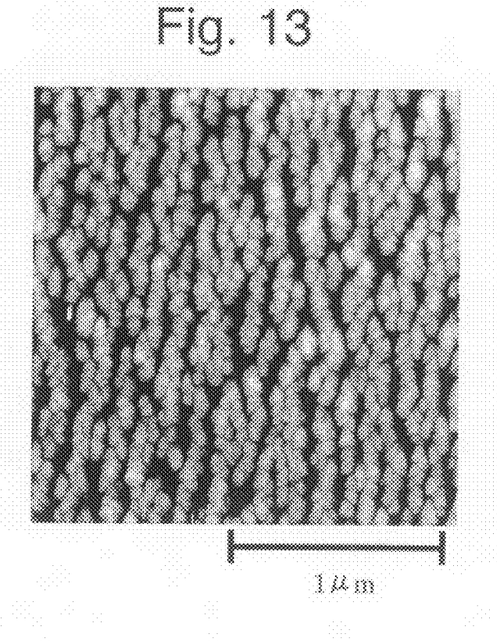
FIG. 13 is an AFM image of a base manufactured with $SiO_2$.

Next, the oblique deposition technique, which is the method for manufacturing an optical sensor in accordance with the present invention, is described with reference to FIG. 13. In the oblique deposition technique, nano-columns 3 are formed on the substrate 2 by using a physical vapor deposition method such as a vacuum evaporation method and sputtering.

Figure 12:
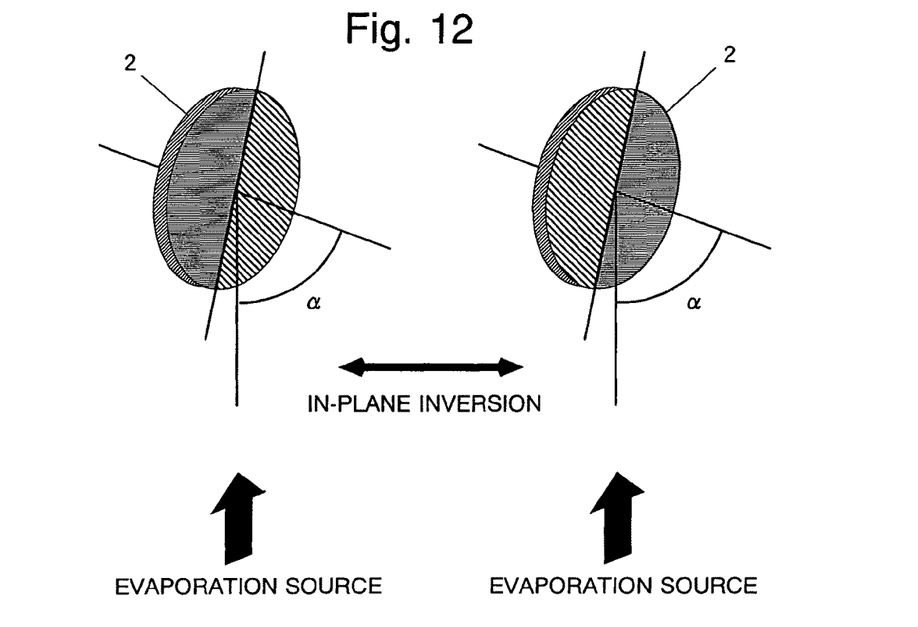
FIG. 12 is a schematic view showing a dynamic deposition method which is a manufacturing method of an optical sensor according to the present invention.

First, the transparent portion's material is deposited on the substrate 2 set at an angle $\alpha$ to the vapor flow's incoming direction of the transparent portion's material as shown on the left side of FIG. 12. When a layer is formed to a certain thickness, in-plane azimuth of the substrate is changed by 180° as shown on the right side of FIG. 12. The base of the nano-column 3 is accordingly formed on the surface of the substrate 2. The tilt angle (deposition angle) $\alpha$ is preferably between 45° and 88°. It is possible to control the aspect ratio of the deposited portion by changing this deposition angle.

If the substrate is periodically turned around after each layer is formed 100 nm or more thick, the nano-columns will be formed in a zigzag shape along the layer thickness direction. Hence, it is preferable to shorten the period to turn around the substrate 2 compared to when generally forming columns using the oblique deposition technique. The turn-around period may preferably be from 5 to 100 nm in general, and be 50 nm or less for normal oxides, although the optimal period depends on the evaporated material. The thin films manufactured in the manner as described earlier has a column structure having an elongated anisotropic shape perpendicular to the deposition surface (substrate surface), unlike the thin films manufactured by a general oblique deposition technique.

In this invention, the aforementioned column structure is used as a base of the nano-column 3; an optical sensor is manufactured by appropriately forming a transparent portion 31 or a noble metal portion 32. FIG. 13 is an AFM (Atomic Force Microscope) image of the surface of a base manufactured with $SiO_2$. It is confirmed that the base has an anisotropic shape.

Figure 14:
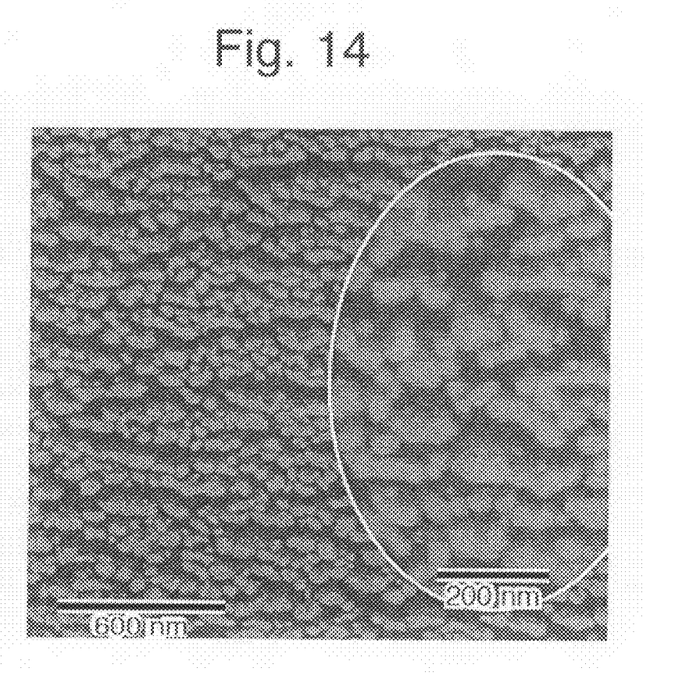
FIG. 14 is a backscattered electron image of the surface of an optical sensor with Ag deposited onto the surface of the base.

When a noble metal is deposited onto the base, the in-plane deposition direction is preferably perpendicular to the longitudinal direction (that is, along the transverse direction) of the nano-column 3. If the deposition angle is set properly, it is then possible to have a noble metal deposited only onto the convex portion of the nano-column 3. The deposition angle is also preferable between 45° and 88°. FIG. 14 is a backscattered electron image of the surface of an optical sensor with Ag deposited onto the surface of the base as in the manner set forth above. Many bright spots are particles of Ag.

The thickness of the noble metal portion 32 needs to be optimized according to the measurement method to be performed, the wavelength of probe light, and other factors. However, the thickness is preferably 50 nm or less; if the thickness is too large, an oblique column structure is formed regardless of the base's shape.

The deposition process of a noble metal can be performed either from two oblique directions by inverting the substrate 2 in-plane as in the manner when a base is prepared, or from one direction without in-plane inversion.

With the oblique deposition technique as previously described, it is possible to obtain a morphologically controlled optical sensor. Since this manufacturing method is extremely simple, the optical sensor can be manufactured at low cost. Sensors with a noble metal multilayer structure have been particularly difficult to manufacture simply, but the oblique deposition technique according to the present invention enables such sensors to be manufactured easily.

An example of manufacturing an optical sensor according to the present invention is subsequently described. In this example, $SiO_2$ was used for the transparent substance and Ag was used for the noble metal.

(1) Corning-7059 glass was used for the substrate. After organically cleaned, the substrate was attached to a vacuum chamber. Then the vacuum chamber was evacuated to $1 \times 10^{-6}$ Torr ($1.33 \times 10^{-4}$ Pa).

(2) An $SiO_2$ pellet was inserted into an electron beam evaporation source which was placed about 50 cm under the substrate. Then the pellet was heated by electron beam irradiation.

(3) The $SiO_2$ was next deposited with a deposition angle of 82°, and with a substrate inverting cycle of 15 nm (inverted every 15 nm deposition thickness). The substrate was inverted 30 times during the deposition to form a base layer (transparent portion) of $SiO_2$.

(4) An Ag pellet was inserted into the electron beam evaporation source placed about 50 cm under the substrate. Then it was heated by electron beam irradiation.

(5) The Ag was obliquely deposited from one direction with a deposition angle of 75° to form an Ag layer with a deposition thickness of 15 mn.

(6) The evaporation source was changed to $SiO_2$ and it was again heated by electron beam irradiation.

(7) The $SiO_2$ was deposited with a deposition angle of 82° and with a substrate inverting cycle of 15 nm. The substrate was inverted 10 times.

(8) Processes (4) through (7) were repeated four times to obtain an optical sensor with a large number of nano-columns which have internal eight-layer noble metal portions.

Figure 15:
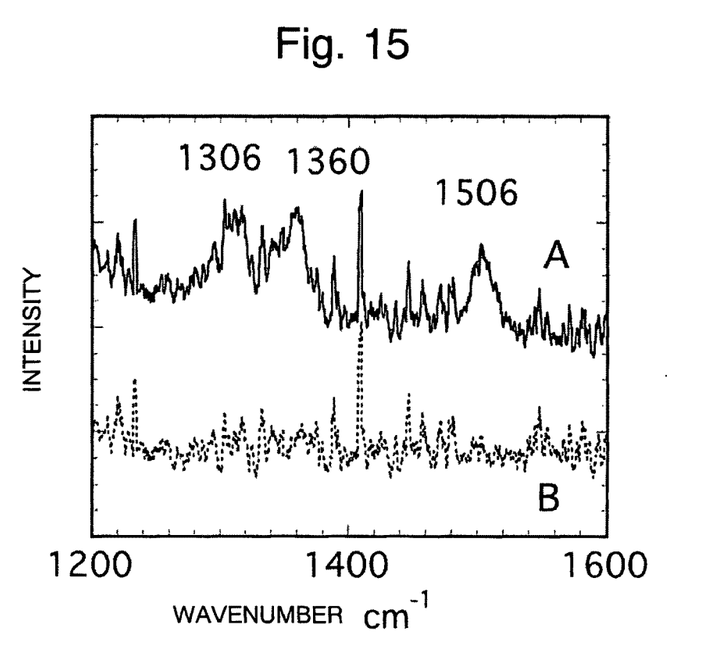
FIG. 15 shows Raman spectra of a rhodamine aqueous solution obtained by an optical sensor according to the present invention (A: when the polarization of the incident light was set along the longitudinal direction of the noble metal portions, B: when the polarization of the incident light was set along the transverse direction of the noble metal portions)

In order to confirm the effects of the present invention, the inventors delivered rhodamine aqueous solution by drops into the optical sensor according to the present invention and measured the Raman spectrum using probe light of 780 nm. FIG. 15 shows the measurement result. In FIG. 15, A (solid line) shows a spectrum obtained when the polarization of the incident light was set along the longitudinal direction of the noble metal portions (nano-columns), and B (dotted line) shows a spectrum obtained when the polarization of the incident light was set along the transverse direction of the noble metal portions. Peaks attributable to rhodamine were observed only in A.

As a comparative example, a substrate having a large number of nano-columns consisting only of transparent portions was used as an optical sensor, but no peaks attributable to rhodamine were observed.

Figure 16:
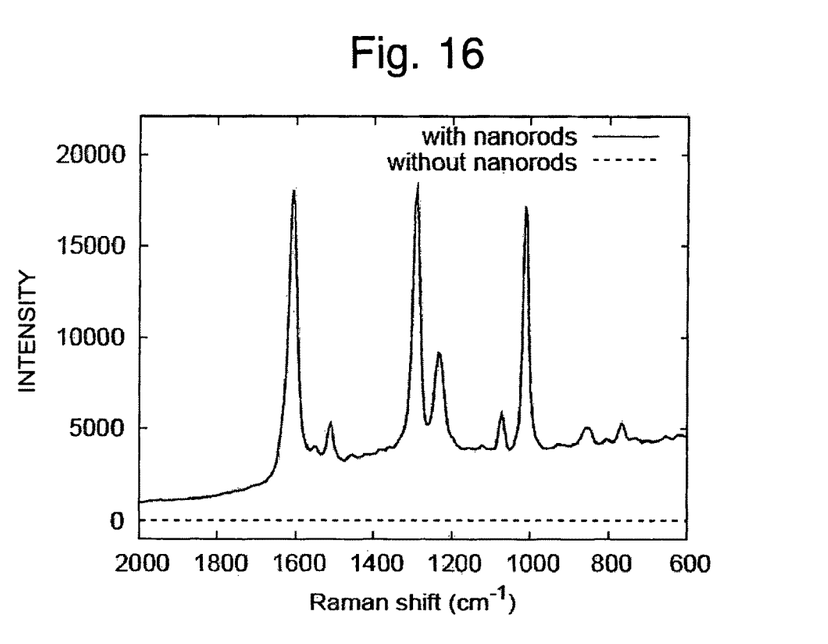
FIG. 16 shows a Raman spectrum of a 4,4-bipyridine aqueous solution obtained by an optical sensor according to the present invention.

In addition, the Raman spectrum of 4,4-bipyridine aqueous solution (1 mmol/l) was measured with an optical sensor according to the present invention. FIG. 16 shows the Raman spectrum measured after the sensor was impregnated with 4,4-bipyridine aqueous solution for 10 minutes. As a comparative example, the Raman spectrum measured with a substrate without nano-columns is shown in FIG. 16. This shows that very noticeable enhancement effects can be achieved with an optical sensor according to the present invention.

When a measurement of Raman light (molecular measurement) is performed with an optical sensor having a large number of nano-columns whose cross section taken substantially parallel to the substrate has an anisotropic shape, such as an optical sensor according to the present invention, as previously described, it is necessary to set the polarization of the incident light along the longitudinal direction of the noble metal portions, or the nano-columns, in order to enhance the sensitivity (enhance the Raman spectral intensity). However, such adjustment must be done by hand with conventional apparatuses, which requires not only time but also the experience of a user. The inventors have advanced the research and have succeeded in developing a Raman light measuring apparatus suitable for optical sensors and capable of solving these problems.

It should be noted that optical sensors which can be used in a Raman light measuring apparatus to be described later are not limited to the sensors according to the present invention or to the sensors which are obtained by a manufacturing method according to the present invention. It is possible to use conventional and general optical sensors having similar configuration.

Figure 17:
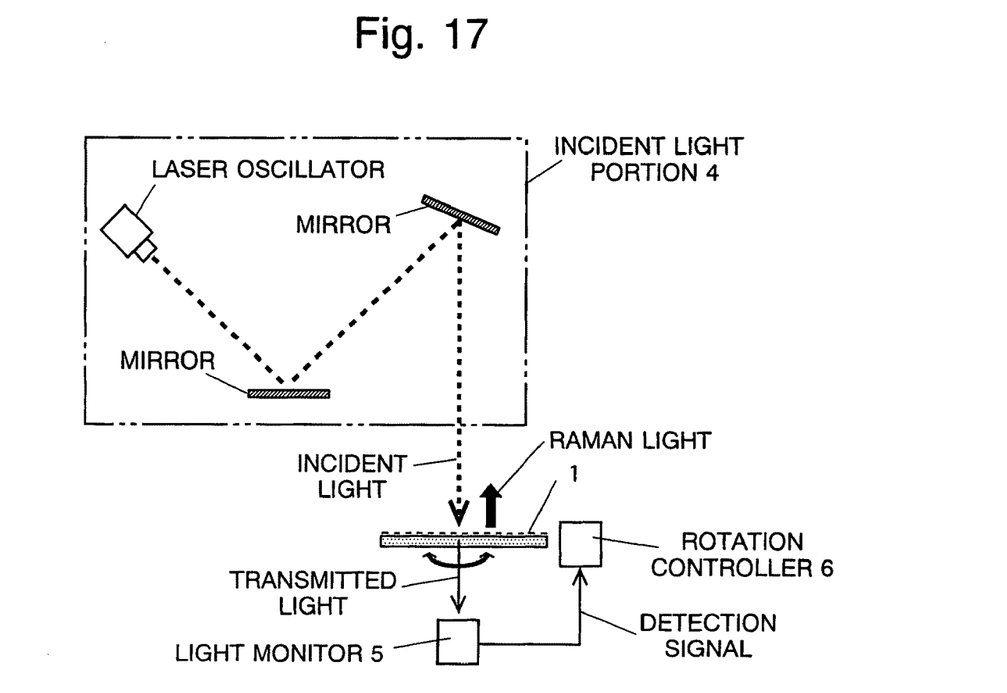
FIG. 17 is a schematic view of an embodiment of a Raman light measuring apparatus for an optical sensor.

One example of a Raman light measuring apparatus for an optical sensor is shown in FIG. 17. A Raman light measurer for measuring the Raman light arising from an optical sensor 1 is not shown in FIG. 17.

With this apparatus, a linearly-polarized laser such as a semiconductor laser is used as an incident light. In an incident light portion 4 which includes a laser oscillator and a mirror, the optical system is configured so that the polarization direction will not change. Here, it is preferable that the polarization of the laser be adjusted to be s-polarized, which has high reflectivity, in order to prevent the lowering of the light intensity.

In the apparatus shown in FIG. 17, if the light is polarized perpendicular to the figure plain for example, the longitudinal direction of the noble metal portion of the optical sensor 1 is also preferably perpendicular to the figure plain. Then, the optical sensor 1 is first placed so that its surface is perpendicular to the incident light. However, the direction of the noble metal portion, which has an elongated shape, is unknown. Therefore, a light monitor 5 such as a photodiode is placed under the optical sensor 1 in the apparatus according to the present invention, to measure the intensity of the transmitted light which has passed through the optical sensor 1 without being absorbed. The light monitor 5 provides a detection signal which shows the intensity of the measured transmitted light to a rotation controller 6. The substrate of the optical sensor 1 is comprised of a transparent material so that the incident light can pass through it.

The rotation controller 6 has a rotator (not shown) which rotates the optical sensor 1 in a plane perpendicular to the incident light. With the rotation of the optical sensor 1, the polarization direction of the incident light and the array direction of the noble metal portion, which is anisotropic, relatively change. Therefore, the amount of the incident light which is absorbed on the surface of the optical sensor 1 varies, and the intensity of the transmitted light varies accordingly. The rotation controller 6 specifies a rotation position of the optical sensor 1 based on the detection signal provided from the light monitor 5 in order to minimize the intensity of the transmitted light measured by the light monitor 5, and determines the specified position to be the optimal measurement position for the optical sensor 1.

The smallest intensity of the transmitted light means the maximum intensity of the Raman light generated in the optical sensor 1. Therefore, it is possible to automatically specify the point where the intensity of the Raman light generated in the optical sensor 1 is maximized with this measuring apparatus. Hence, the measuring apparatus can greatly save the trouble of the setup.

Figure 18:
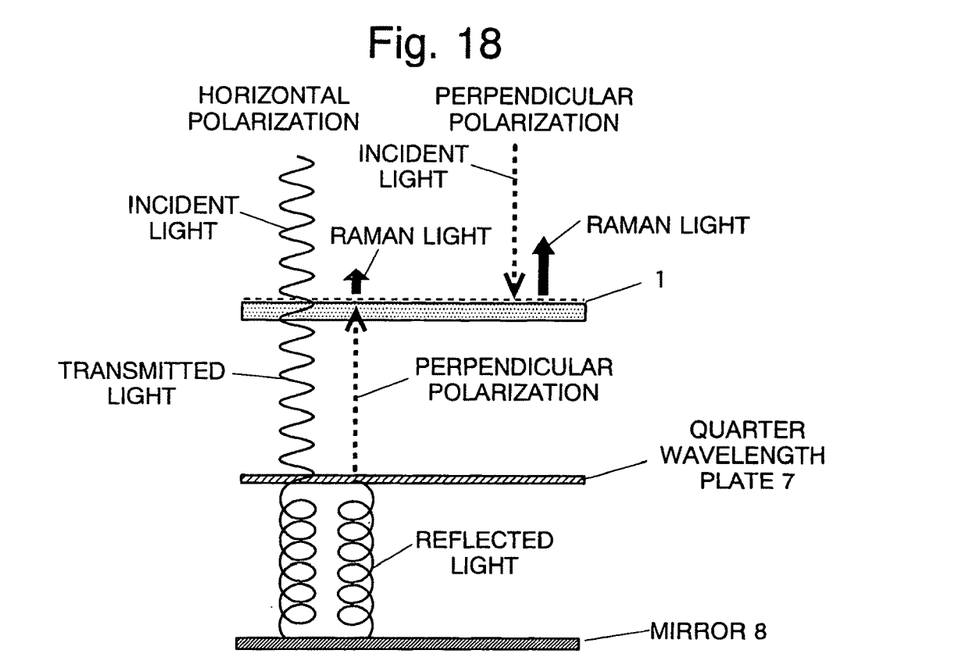
FIG. 18 is a schematic view of another embodiment of a Raman light measuring apparatus for an optical sensor.

Another example of a Raman light measuring apparatus for an optical sensor according to the present invention is shown in FIG. 18. An incident light portion 4 and a Raman light measurer are not shown in FIG. 18.

The linear polarization degree of a laser, which is an incident light, may not be very high, depending on the kind or the performance of the laser oscillator. In such cases, even if the longitudinal direction of the noble metal portion on the surface of the optical sensor 1 is parallel to the main polarization direction of the incident light, not all the incident light is absorbed on the surface of the optical sensor 1. There is some incident light (or transmitted light) which passes through the optical sensor 1 without being absorbed and does not contribute to the Raman light enhancement.

In an optical sensor according to the present embodiment, a quarter wavelength plate 7 and a mirror 8 which is placed under it are placed under the optical sensor 1 which has a substrate comprised of an optically-transparent material. Here "under" means the direction of the incident light. The quarter wavelength plate 7 may be a commonly-used wave plate or phase difference film, and is placed so that the direction of its main axis measures 45° with the polarization direction of the linear-polarized laser which is emitted from the incident light portion 4 (not shown). The mirror 8 preferably can be one having high reflectivity as a dielectric mirror or similar mirrors.

Suppose that the longitudinal directions of the noble metal portions of the optical sensor 1 are aligned almost perpendicular to the figure plain in the measuring apparatus shown in FIG. 18. Here, the incident light whose polarization direction is almost perpendicular to the figure plain (right portion of FIG. 8) is absorbed on the surface of the optical sensor 1 and contributes to the generation of Raman light. On the other hand, most of the incident light whose polarization direction is almost horizontal to the figure plain (left portion of FIG. 8) passes through the optical sensor 1 without being absorbed. As the transmitted light moves on and passes through the quarter wavelength plate 7, its polarization is converted to a circular polarization. As it further moves on and is reflected by the mirror 8, the polarization direction is inverted, and as it passes through the quarter wavelength plate 7 once more, the polarization direction eventually becomes perpendicular to the figure plate. The light reaches the noble metal portions of the surface of the optical sensor 1 via the undersurface of the optical sensor 1, contributing to the generation of Raman light.

As just described, with the measuring apparatus according to the present embodiment, the incident light with a polarization which passes thorough the optical sensor 1 at the time when it is incident is not wasted but absorbed in the optical sensor 1. Therefore, the Raman light intensity is enhanced.

The optical sensor 1, the quarter wavelength plate, and the mirror 8 are interspatially placed in FIG. 8, but it is possible that a part or all of them can be integrated.

Figure 19:
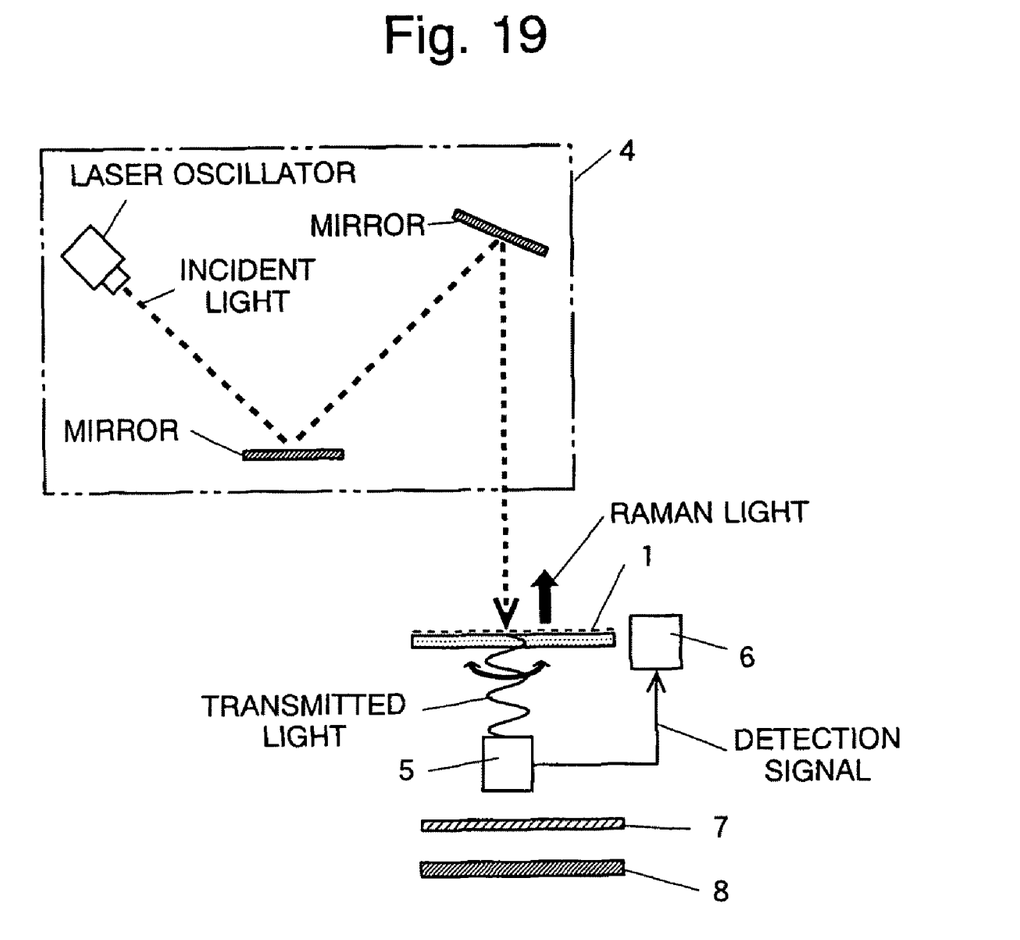
FIG. 19 is a schematic view of another embodiment of a Raman light measuring apparatus for an optical sensor.

As a further preferable Raman light measuring apparatus for an optical sensor, it is possible to combine the two examples of Raman light measuring apparatus which were previously described. In this configuration, for example, the light monitor 5 is placed between the optical sensor 1 and the quarter wavelength plate 7 (can be placed between the quarter wavelength plate 7 and the mirror 8) as shown in FIG. 19. Then the optimal position for the optical sensor 1 is determined by the rotation controller 6. And then, the light monitor 5 or the incident light is moved to prevent the transmitted light from being interrupted, and a measurement is initiated. With this, it is possible to obtain a higher Raman light intensity.

An optical sensor, a method for manufacturing the optical sensor, and a Raman light measuring apparatus for the optical sensor according to the present invention were described thus far. It should be noted that the above-described embodiments are merely examples, and it is evident that they can be changed or modified as needed.

The invention claimed is:

1. A Raman light measuring apparatus for molecular measurement, comprising:
   an optical sensor including:
   a substrate: and
   a large number of anisotropic nano-columns, which are formed on the substrate, whose cross section taken substantially parallel to the substrate has a predetermined aspect ratio, wherein:
   each of the nano-columns includes a combination of a transparent portion and a noble metal portion having an anisotropic shape according to a shape of each nano-column and being formed at least on top of or in an intermediate portion of each of the nano-columns; and
   the large number of nano-columns are aligned so that their longitudinal direction of cross section taken substantially parallel to the substrate are substantially straight or substantially parallel; and
   a light irradiator configured to irradiate a linearly polarized laser perpendicularly to a surface of the optical sensor;
   a transmitted light monitor configured to measure an intensity of a transmitted light which has passed through the optical sensor; and
   a rotation controller configured to rotate the optical sensor in a plane which is perpendicular to an irradiated light so that the intensity of the transmitted light measured by the transmitted light monitor is minimized.

2. A Raman light measuring apparatus for molecular measurement, comprising:
   an optical sensor including:
   a substrate; and
   a large number of anisotropic nano-columns, which are formed on the substrate, whose cross section taken substantially parallel to the substrate has a predetermined aspect ratio, wherein:
   each of the nano-columns includes a combination of a transparent portion and a noble metal portion having an anisotropic shape according to a shape of each nano-column and being formed at least on top of or in an intermediate portion of each of the nano-columns; and
   the large number of nano-columns are aligned so that their longitudinal direction of cross section taken substantially parallel to the substrate are substantially straight or substantially parallel; and
   a light irradiator configured to irradiate a linearly polarized laser perpendicularly to a surface of the optical sensor;
   a quarter wavelength plate being placed under the optical sensor so that a principle axis makes an angle of 45° with a polarization direction of the linearly polarized laser; and
   a mirror being placed under the quarter wavelength plate.

3. The Raman light measuring apparatus according to claim 2, further comprising:
- a transmitted light monitor, which is placed between the optical sensor and the mirror, and is configured to measure an intensity of a transmitted light which has passed through the optical sensor; and
- a rotation controller configured to rotate the optical sensor in a plane which is perpendicular to an irradiated light so that the intensity of the transmitted light measured by the transmitted light monitor is minimized.

4. A Raman light measuring apparatus for molecular measurement, comprising:
- an optical sensor including:
  - a substrate; and
  - a large number of anisotropic nano-columns, which are formed on the substrate, whose cross section taken substantially parallel to the substrate has a predetermined aspect ratio, wherein:
- each of the nano-columns includes a combination of a transparent portion and a noble metal portion having an anisotropic shape according to a shape of each nano-column and being formed at least on top of or in an intermediate portion of each of the nano-columns;
- the large number of nano-columns are aligned so that their longitudinal direction of cross section taken substantially parallel to the substrate are substantially straight or substantially parallel; and
- the noble metal portion is made of any one of Au, Ag and Cu; and
- a light irradiator configured to irradiate a linearly polarized laser perpendicularly to a surface of the optical sensor;
- a transmitted light monitor configured to measure an intensity of a transmitted light which has passed through the optical sensor; and
- a rotation controller configured to rotate the optical sensor in a plane which is perpendicular to an irradiated light so that the intensity of the transmitted light measured by the transmitted light monitor is minimized.

5. A Raman light measuring apparatus for molecular measurement, comprising:
- an optical sensor including:
  - a substrate; and
  - a large number of anisotropic nano-columns, which are formed on the substrate, whose cross section taken substantially parallel to the substrate has a predetermined aspect ratio, wherein:
- each of the nano-columns includes a combination of a transparent portion and a noble metal portion having an anisotropic shape according to a shape of each nano-column and being formed at least on top of or in an intermediate portion of each of the nano-columns;
- the large number of nano-columns are aligned so that their longitudinal direction of cross section taken substantially parallel to the substrate are substantially straight or substantially parallel; and
- the noble metal portion is made of any one of Au, Ag and Cu; and
- a light irradiator configured to irradiate a linearly polarized laser perpendicularly to a surface of the optical sensor;
- a quarter wavelength plate being placed under the optical sensor so that a principle axis makes an angle of 45° with a polarization direction of the linearly polarized laser; and
- a mirror being placed under the quarter wavelength plate.

6. The Raman light measuring apparatus according to claim 5, further comprising:
- a transmitted light monitor, which is placed between the optical sensor and the mirror, and is configured to measure an intensity of a transmitted light which has passed through the optical sensor; and
- a rotation controller configured to rotate the optical sensor in a plane which is perpendicular to an irradiated light so that the intensity of the transmitted light measured by the transmitted light monitor is minimized.

* * * * *